(12) United States Patent
Zawaideh et al.

(10) Patent No.: US 12,306,092 B2
(45) Date of Patent: May 20, 2025

(54) IMAGING SPECTROPOLARIMETER AND SAMPLE CHARACTERIZATION METHODOLOGY UTILIZING THE SAME

(71) Applicant: Bruker Nano, Inc., Santa Barbara, CA (US)

(72) Inventors: Mazen Zawaideh, Carlsbad, CA (US); Chris Claypool, Carlsbad, CA (US); Emad Zawaideh, Carlsbad, CA (US)

(73) Assignee: BRUKER NANO, INC., Goleta, CA (US)

( * ) Notice: Subject to any disclaimer, the term of this patent is extended or adjusted under 35 U.S.C. 154(b) by 350 days.

(21) Appl. No.: 17/979,427

(22) Filed: Nov. 2, 2022

(65) Prior Publication Data

US 2023/0057928 A1  Feb. 23, 2023

Related U.S. Application Data

(63) Continuation-in-part of application No. 16/219,618, filed on Dec. 13, 2018, now Pat. No. 11,499,870, which is a continuation-in-part of application No. 14/121,491, filed on Sep. 11, 2014, now abandoned.

(51) Int. Cl.
*G01N 21/21*  (2006.01)
*G01N 21/95*  (2006.01)
*G01N 33/483* (2006.01)

(52) U.S. Cl.
CPC ......... *G01N 21/21* (2013.01); *G01N 21/9501* (2013.01); *G01N 33/4833* (2013.01)

(58) Field of Classification Search
CPC . G01N 21/21; G01N 21/9501; G01N 33/4833
See application file for complete search history.

(56) References Cited

U.S. PATENT DOCUMENTS

| | | | |
|---|---|---|---|
| 5,889,592 A | 3/1999 | Zawaideh | |
| 5,999,267 A | 12/1999 | Zawaideh | |
| 7,557,918 B1 | 7/2009 | Newman et al. | |
| 8,320,996 B2 * | 11/2012 | Panasyuk | G01N 21/21 600/407 |
| 8,618,470 B2 * | 12/2013 | Dantus | G01N 21/21 250/252.1 |

(Continued)

OTHER PUBLICATIONS

Abelès, Research on the Propagation of Electromagnetic Waves in Stratified Media—Application to Thin Films, Annuals of Physics, 1950, 5(596) [No English Language Translation Available].

(Continued)

*Primary Examiner* — Dani Fox
*Assistant Examiner* — Fani Polyzos Boosalis
(74) *Attorney, Agent, or Firm* — Quarles & Brady LLP; Yakov Sidorin (57) ABSTRACT

An imaging spectropolarimeter configured to examine targets with polarized light, in which orientation of light-polarizing components is judiciously chosen to be target-specific and which employ a three-camera optical detection system defining an optical detection axis with respect to which individual camera analyzers are oriented in a specifically-defined fashion. Programmable electronic circuitry is adapted to substantially simultaneously acquire polarimetric images of the target utilizing intensity information collected by the multi-pixel sensors of the optical detection system.

11 Claims, 7 Drawing Sheets

(56) References Cited

U.S. PATENT DOCUMENTS

| | | |
|---|---|---|
| 2012/0050533 A1 | 3/2012 | Dewa et al. |
| 2012/0183175 A1 | 7/2012 | Alouini et al. |
| 2015/0219497 A1 | 8/2015 | Johs et al. |
| 2016/0054343 A1* | 2/2016 | Holmes ................ G01N 35/026 422/65 |

OTHER PUBLICATIONS

Chung et al., Use of Polar Decomposition for the Diagnosis of Oral Precancer, Applied Optics, 2007, 46 (15):3038-3045.

Daukantas, Using Optics to Detect Skin Cancer, Optics & Photonics News, 2007, 18(11):28-33.

Demos et al., Deep Subsurface Imaging in Tissues Using Spectral and Polarization Filtering, Optics Express, 2000, 7 (1):23-28.

Gambichler et al., In Vivo Optical Coherence Tomography of Basal Cell Carcinoma, Journal of Dermatological Science, 2007, 45(3):167-173.

Ghosh et al., Tissue Polarimetry: Concepts, Challenges, Applications, and Outlook, Journal of Biomedical Optics, 2011, 16(11):110801, pp. 1-29.

Jacques et al., Imagining Skin Pathology with Polarized Light, Journal of Biomedical Optics, 2002, 7(3):329-340.

Jacques et al., Polarized Light Camera to Guide Surgical Excision of Skin Cancers, Photonic Therapeutics and Diagnostics IV, 2008, 6842, pp. 1-7.

Oh et al., Three-Dimensional Imaging of Skin Melanoma in Vivo by Dual-Wavelength Photoacoustic Microscopy, Journal of Biomedical Optics, 2006, 11(3):034032, pp. 1-4.

Pierangelo et al., Multispectral Mueller Polarimetric Imaging Detecting Residual Cancer and Cancer Regression after Neoadjuvant Treatment for Colorectal Carcinomas, Journal of Biomedical Optics, 2013, 18(4):046014, pp. 1-9.

Rajaram et al., Clinical Instrument for Spectral Diagnosis of Cutaneous Malignancy, Advanced Biomedical and Clinical Diagnostic Systems VI, 2008, 6848, pp. 1-10.

Safrani et al., Skin Biomedical Optical Imaging System Using Dual-Wavelength Polarimetric Control with Liquid Crystals, Journal of Biomedical Optics, 2010, 15(2):026024, pp. 1-8.

Tyo et al., Review of Passive Imaging Polarimetry for Remote Sensing Applications, Applied Optics, 2006, 45(22):5453-5469.

* cited by examiner

IMAGING SPECTROPOLARIMETER AND SAMPLE CHARACTERIZATION METHODOLOGY UTILIZING THE SAME

CROSS-REFERENCE TO RELATED APPLICATIONS

This patent application is a continuation-in-part of U.S. patent application Ser. No. 16/219,618 filed on Dec. 13, 2018 and now published as US 2020/0191657, which is a continuation-in-part of U.S. patent application Ser. No. 14/121,491 filed on Nov. 9, 2014, which claims the benefit of the U.S. Provisional Patent Application No. 61/876,354 filed on Sep. 11, 2013. The disclosure of each of the above-identified patent documents is incorporated by reference herein.

TECHNICAL FIELD

The present invention generally relates to measurement systems and methods and, in particular to polarimetric systems and methods for use in non-invasive imaging for diagnostics of target objects, whether including biological tissue or inanimate.

RELATED ART

Detecting and treating cancer remains one of the biggest challenges in modern medicine, and characterization of material samples in semiconductor industry remain of critical importance with ever-increasing spatial density of devices manufacture per unit of surface area experienced with industrial transition from deep UV-lithography (utilizing light at 193 nm, for example) to extreme UV lithography (utilizing light at 38 nm or even 13.5 nm).

Biopsy, for example, has been the standard for making definitive cancer diagnosis and includes medical removal of a tissue sample, followed by the analysis of thin slices of excised tissue under a microscope. In recent years optical techniques have received considerable attention for tissue diagnostics because these methods tend to be minimally or non-invasive, fast, and inexpensive. The term "optical biopsy" is commonly used to indicate a form of optical measurement to non-invasively perform a tissue diagnosis, in situ, in vivo, and in real time. The motivation for implementation of optical biopsy procedures is to guide and/or possibly eliminate the need for surgical removal of biopsy tissue samples by, instead, recording images of the tissue in question and attempting a diagnosis of such tissue based on the optical measurements. Additional drivers of this methodology are the potential for reduced health care costs due to minimizing histology, and—in some cases—at least substantially reduce the need for the surgical environment required for acquiring biopsy samples. While the ultimate goal of these optical methods is to eliminate the need for removing tissue samples, an intermediate goal during early clinical phases of these optical technologies is at least to provide guidance in locating the optimum sites for biopsy. Additionally, optical methods can serve as an aid in surgical procedures by helping the operator to identify tumor margins in real time.

Semiconductor industry experiences its own challenges. The drive for ever more powerful microprocessors and greater memory storage places demands on all steps of the semiconductor wafer fabrication process. At some point, incremental improvements are no longer sufficient, and further device shrinking requires a completely different technology. The semiconductor industry is now experiencing this with lithography, where extreme ultraviolet (EUV) lithography is replacing 193 nm immersion (193i) lithography for more and more critical chip layers. Major manufacturers are using EUV lithography for volume production of advanced logic devices now. But even though the technology is in production, there are hurdles to overcome, one of which is the ability to precisely and on a very small spatial scale characterize structure and/or defects in material samples such as semiconductor wafers.

The primary physical characteristics associated with an optical field are intensity, wavelength, coherence, and polarization. In general, spectral information provides data about the molecular makeup of the material investigated with the use of an optical field, while polarization information provides structural data—such as those about surface features, shape, shading, and roughness, to name just a few (see, for example, J. S. Tyo, et al., "Review of passive imaging polarimetry for remote sensing applications," Appl. Opt. 45(22), 5453-5469 (2006).) Assessment of polarization tends to provide information that is largely uncorrelated with spectral and intensity images. As a result, spectropolarimetric imaging is in a position to provide information about both the material make up and morphology of the sample. In addition, spectropolarimetric imaging measurements enhanced visualization of superficial structures to allow for sub-surface imaging (see: J. Chung, et al., "Use of polar decomposition for the diagnosis of oral precancer," Appl. Opt. 46(15), 3038-3044 (2007).). Because the absorption characteristics of tissue results in a wavelength-dependent penetration depth of tissue-interrogating light, multispectral polarimetric imaging allows different layers of the tissue sample to be imaged, ranging from those located at about 50 microns depth for UV wavelengths to those at about 1000 microns depth for the NIR wavelengths.

The spectropolarimetric imaging method has several advantages over other optical methods—at least as far as the tissue diagnostics is concerned. In comparison with confocal microscopy, OCT, and photo-acoustic microscopy methods, for example, it is much faster and cheaper. In comparison with light scattering spectroscopy methods, it provides a visualization of the tissue sample or lesion. And in comparison with polarimetric imaging, spectropolarimetric imaging possesses an additional degree of freedom in providing spectrally resolved images with improved image contrast due to different absorption and scattering characteristics of benign and malignant tissues.

Figure 1:
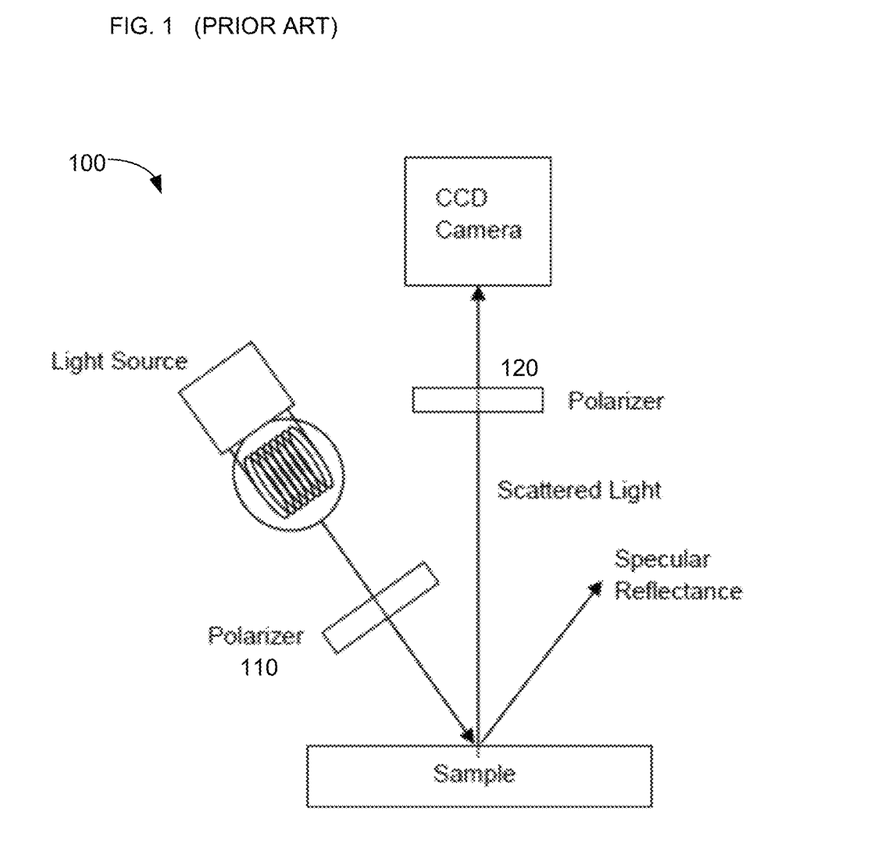
FIG. 1 shows schematically a conventional imaging polarimeter system.

The most common experimental configuration 100 of a conventional polarimetric imaging system is shown in FIG. 1. The two most common methods that define the state of related art for the polarimetric imaging technique are orthogonal state contrast polarimetric measurements and Mueller matrix measurements.

In the orthogonal state contrast measurement methodology, the camera is used to acquire two images. The first image is acquired when the polarizer is oriented to accept light having polarization substantially parallel to that of the incident light (Ipar), and the second image is acquired with the polarizer oriented to accept light that has polarization substantially perpendicular to that of the incident light (Iper). That is, in reference to FIG. 1, for orthogonal state contrast measurements, the polarizer in front of the camera is oriented to select light with a state of polarization that is either parallel or perpendicular to that of the incident light to yield two images that are then mathematically combined to yield an "orthogonal polarization" image.

Specifically, the two empirically acquired images are then used to create a third image, referred to as the orthogonal polarization image (Ipol), with irradiance distribution according to the equation below:

$$I_{pol} = \frac{I_{par} - I_{per}}{I_{par} + I_{per}}$$

Although simple orthogonal state contrast polarimetric measurements produce images with higher contrast and improved tissue imaging resolution (as compared to image acquired with the use of unpolarized light), the resulting orthogonal state contrast polarimetric images provide only a small portion of the polarimetric information content available, and do not resolve what is present in deeper regions of the imaged tissue.

Methodology employing the Mueller matrix for polarimetric imaging utilizes dual rotating polarizers configured according to the scheme devised by Azzam (see: R. M. Azzam and N. M. Bashara, *Elhpsometry and Polarized Light*; Elsevier, 1987) For the intended measurements, both polarizers 110, 120 of the system 100 are rotated independently to acquire at least 16 images at different angles of orientation of the transmission axes of the polarizers to create the 4×4 matrix representing the target sample (object). The addition of a spectral filter (such as a color filter wheel) between the light source and the sample may allow for polarimetry measurements at discreet wavelengths.

The 4×4 Mueller matrix mathematically relates how interaction of the incident light with the sample affects the polarization vector of the incident light beam, and can be used to describe the polarization properties of a sample. There are 16 degrees of freedom in the Mueller matrix and therefore a minimum of 16 images are required to determine an arbitrary unknown sample matrix. Although the experimental Mueller matrix of a tissue sample contains information on retardance, attenuation, and depolarization of light, this information is not readily apparent in the original 16 images and the experimental polarimetric images are difficult to interpret directly. In the sample were a clear medium with defined optical interfaces, electromagnetic theory with Maxwell's equations can be used for polarimetry analysis. However, tissue is a turbid medium with complex dielectric structures and this type of analysis is impractical and not currently feasible. Instead, the sample discriminating parameters are typically extracted using a variety of polar decomposition methods. Even with these decomposition methods, Mueller matrix image analysis still remains exceedingly complex for biological tissue samples.

The methodologies currently employed in related art are subject to several additional limitations. For example, currently used methods ignore specular reflection and measure scattered light only. There is a potential wealth of additional information content that can be gains by collecting spectropolarimetric images in both specular and non-specular mode. Furthermore, as a skilled person will appreciate, multiple scattering of light in thick tissues leads to the depolarization of light, thereby creating a strong source of optical noise (represented by the so-depolarized light) that, effectively, hinders the detection of the remaining information-carrying weak (in comparison) polarization signal. As a result, it is necessary to maximize measurement sensitivity in order to further enhance image resolution and contrast.

In order to perform tissue diagnostics in situ, in vivo, and in real time the polarization and wavelength must be scanned/varied fast enough to prevent image blurring from unintentional relative movements between the sample and the interrogating beam of light. However, fast data acquisition, as known, is very difficult to achieve when utilizing Mueller matrix methods with rotating polarizers for spectropolarimetric imaging.

Furthermore, the system and method should have potential for compactness and miniaturization (in order to minimize cost and ease of use). This is especially critical in the context of endoscopically-guided procedures, in which small foot-print of the device is necessary to ensure ability to traverse narrow luminal diameters (e.g., respiratory or gastrointestinal tract).

There remains a need, therefore, in a better imaging spectrometer that is operationally-fast and easy to use and possesses imaging of tissue and its underlying structure with higher contrast and higher resolution than those of existing methodologies

SUMMARY OF THE INVENTION

The present invention provides a measurement system and method for fast spectropolarimetric imaging with improved contrast and higher resolution imaging of tissue and its underlying structure. Although the primary application of the proposed methodology is for non-invasive biomedical diagnostics, the invention could have applications in many fields of optical metrology ranging from remote sensing to industrial monitoring.

In particular, the invention provides a material characterization apparatus that includes a holder device configured to house material contents and an imaging spectropolarimeter. The imaging spectropolarimeter generally contains (a) a light source configured to generate polarized light (such light source includes an optical spectral filter configured to define a desired spectral range of said polarized light and a source polarizer having a transmission axis oriented at a polarizer angle with respect to a chosen axis; here, the polarizer angle is defined within a range from about 18 degrees to about 25 degrees and is necessarily dependent on a refraction index of the material contents); (b) an optical detection system; and (c) programmable electronic circuitry. The optical detection system in turn, contains i) a first optical camera unit that includes a first camera polarizer configured to have a first transmission axis o be substantially co-linear with the chosen axis, a first lens, and a first optical sensor, ii) a second optical camera unit that includes a second camera polarizer configured to have a second transmission axis thereof to be tilted by substantially 45° to the chosen axis, a second lens, and a second optical sensor, iii) a third optical camera unit that includes a third camera polarizer configured to have a third transmission axis thereof to be at substantially 90° with respect to the chosen axis, a third lens, and a third optical sensor. Furthermore, the imaging spectropolarimeter includes an optical delivery system configured to receive at least a portion of the polarized light and to redirect light from the at least a portion of such polarized light to each of the first, second, and third optical camera units. The programmable electronic circuitry is operably connected to the optical detection system and a computer usable tangible non-transitory storage medium, while the storage medium has computer readable program code thereon. The computer readable program code includes:—program code for acquiring first, second, and third optical data respectively representing first, second, and third spatial distributions of intensities of portions of light received by the first, second, and third optical sensors;

and—program code for generating, based on said first, second, and third optical data, first, second, and third polarimetric images of the material contents of the holder. Here, the holder device is disposed in optical communication with the lights source and the optical delivery system; the material characterization apparatus is configured to acquire the first, second, and third optical data substantially simultaneously and/or generate the first, second, and third polarimetric images substantially simultaneously, and is also configured as a non-invasive biomedical diagnostic system or as a semiconductor material inspection system.

In at least one implementation, when material characterization apparatus is configured as the non-invasive biomedical diagnostic system—the contents of the holder include a biological tissue, and the program code for generating includes program code for generating images representing cancer detection and/or screening in such biological tissue; or, alternatively, when the apparatus is configured as a semiconductor material inspection system—the contents of the holder include a semiconductor material, and the program code for generating includes program code for generating an image representing a structural defect and/or a geometrical parameter and/or a material content of such semiconductor material. Substantially in every embodiment the light source may be configured to generate a broadband light having a spectral bandwidth including UV light, visible light, and IR light; and/or the material characterization apparatus may be additionally equipped with a repositioning system configured to mutually reposition the light source and the optical detection system to have the optical detection system acquire light that is contained i) only in a specular reflection of the polarized light originated at the contents of the holder, or ii) only in a non-specular reflection of the polarized light originated at the contents of the holder. Alternatively or in addition, and substantially in every embodiment of the invention, the spectropolarimeter of the apparatus may include a zoom lens associated with at least one of the first, second, and third optical camera units (such zoom lens being configured to change a field of view perceived by a corresponding optical sensor); and, in a specific implementation of the latter, the zoom lens may be optionally configured to define a spatial resolution of the polarimetric images to be a micron-scale resolution. Alternatively or in addition, and substantially in every embodiment of the apparatus, the optical delivery system may include first and second optical beam splitters and/or the optical detection system may be structured as a three-camera optical detection system. Alternatively or in addition, the programmable electronic circuitry may be configured to convert pixel intensity data received from the first, second, and third optical sensors into at least four sets of images for each type of contents of the holder.

Embodiments of the invention additionally provide a method that includes a step of using any of the embodiments of the apparatus identified above; a step of receiving polarized light, delivered from the light source of the apparatus, at the material contents of the holder of the apparatus (which material contents include a semiconductor material); a step of substantially simultaneously acquiring light that has interacted with the material contents of the holder and that has been redirected to the optical detection system only specularly or only non-specularly, at each of the first, second, and third optical sensors; and a step of generating—with the use of the programmable electronic circuitry of the apparatus—first, second, and third polarimetric images of the semiconductor material. Here, each of the first, second, and third polarimetric images contains data necessarily represents at least one of a structural defect, a geometrical parameter, or a material composition of such semiconductor material. In at least one implementation, the method may additionally include a step of varying a field of view subtended by at least one of the first, second, and third optical sensors of the apparatus to define a spatial resolution of a corresponding of the first, second, and third polarimetric images to be a micron-scale resolution; and/or a step of converting pixel intensity data received from the first, second, and third optical sensors into at least four sets of images of the semiconductor material.

BRIEF DESCRIPTION OF THE DRAWINGS

The invention will be more fully understood by referring to the following Detailed Description of Specific Embodiments in conjunction with the Drawings, of which.

Generally, the sizes and relative scales of elements in Drawings may be set to be different from actual ones to appropriately facilitate simplicity, clarity, and understanding of the Drawings. For the same reason, not all elements present in one Drawing may necessarily be shown in another.

DETAILED DESCRIPTION

Elements of the Design of an Embodiment of the Invention.

For details of a polarizer-sample-compensator-analyzer (PSCA) experimental configuration providing basic possibilities for a photometric measurement, the reader is respectfully referred to R. M. Azzam and N. M. Bashara, in *Ellipsometry and Polarized Light, Elsevier,* 1987.

As known in related art, light intensities are measured with two optical polarizers spatially oriented such that orientations of their transmission axes correspond to several judiciously chosen azimuth values. (Often, these two optical elements are referred to as polarizer and analyzer: the polarizer being an optical device configured to convert target light into polarized light and the analyzer being a device used to determined whether light is polarized or not). Since the analyzed state of polarization is independent from absolute values of light intensities, one of the states of polarization can be used as a reference for the measurement of relative values. Consequently, at least three independently measured intensity values are required to determine the two real ellipsometric parameters Psi ($\psi$) and Delta ($\Delta$) for a fixed azimuth at angle P, the intensity I(A) at angle A transmitted by the analyzer as according to:

$$I(A)=I(P)|rs|^2 \cos^2 P(\tan^2\psi \cos^2 A+\tan^2 P \sin^2 A+2 \tan\psi \cos\Delta \tan P \cos A \sin A)$$

where $\Delta=\Delta_{sample}-\delta_{compensator}$, and $\delta_{compensator}$ is the retardance of the compensator of the optical scheme (that is, an optical device configured to import a particular path difference to chosen light beams).

Taking the value of intensity corresponding to $A=\pi/2$ as the reference:

$I(\pi/2)=I(P)|rs|^2\cos^2 P (\tan^2 P)$, the ellipsometric angle $\psi$ is obtained from the relative intensity measured for $A=0$:

$$I(0) = I(P)|rs|^2\cos^2 P \left(\tan^2\psi\right)$$

where:

$$\tan\psi = |\tan P|\sqrt{I(0)/I\left(\frac{\pi}{2}\right)}$$

The third value of intensity can be empirically acquired with $A=\pi/4$:

$$I(\pi/4)=\tfrac{1}{2} I(P)|rs|^2\cos^2 P(\tan^2\psi+\tan^2 P+2 \tan\psi \cos\Delta \tan P)$$

This provides the following explicit result for the ellipsometric angle $\Delta$, $$\cos\Delta = \mathrm{sgn}(P)\left[2I(\pi/4) - I(0) - I(\pi/2)\right]/\left[2\sqrt{I(0)I\left(\frac{\pi}{2}\right)}\right]$$

The existing limitation of the current state of the art, which the person of skill will recognize, is the impossibility of distinguishing the sign of $\Delta$ (the value of which is confined to an interval of $\pi$). The azimuth P of the polarizer is the disposable quantity in this scheme; it should be chosen properly to minimize measurement errors. The analysis of the uncertainties in $\psi$ and $\Delta$ in the following section suggests the favorable setting of $P=\psi$, for which $I(0)\approx I(\pi/2)$. In any case, the values of P close to either zero or $\pm\pi/2$ should be avoided, since they lead to a rapid loss of sensitivity. Notably, in the above discussion a possible polarization sensitivity of the detector has been neglected; if present, it can be measured and accounted for using a sample with known parameters, or straight-through operation with no sample.

Improving Experimental Sensitivity of the PSCA Setup.

Analysis of the uncertainties in $\psi$ and $\Delta$, according to the idea of the invention, can be performed to optimize the operation of the proposed design. Using the well-known forms for the normalized Fourier coefficients $$I = I_0[(1 - \cos 2P\cos 2\psi) + (\cos 2P - \cos 2\psi)\cos 2A + (\sin 2P\sin 2\psi\cos\Delta)\sin 2A]$$

$$\alpha = \frac{\cos 2P - \cos 2\Psi}{1 - \cos 2P\cos 2\Psi}$$

$$\beta = \frac{\sin 2\Psi\cos\Delta\sin 2P}{1 - \cos 2P\cos 2\Psi}$$

$$\alpha = \frac{\tan^2\Psi - \tan^2 P}{\tan^2\Psi + \tan^2 P}$$

$$\beta = \frac{2\tan\Psi\cos\Delta\tan P}{\tan^2\Psi + \tan^2 P}$$

$$\tan\Psi = \sqrt{\frac{1+\alpha}{1-\alpha}}|\tan P|$$

$$\cos\Delta = \frac{\beta}{\sqrt{1-\alpha^2}}$$

where $\alpha$ and $\beta$ can be calculated from the experimentally measured intensities according to $$\alpha = \frac{I_0 - I_{90}}{I_0 + I_{90}}$$

$$\beta = 2\left(\frac{I_{45}}{I_0 + I_{90}}\right) - 1$$

With the above expressions, it is now possible to investigate the uncertainties $\delta\psi$ and $\delta\Delta$ in $\psi$ and $\Delta$, respectively, as functions of the uncertainties of the Fourier coefficients. The uncertainties $\delta\psi$ and $\delta\Delta$ represent the fluctuations of $\psi$ and $\Delta$ about their ideal values.

$$\sec^2\Psi\frac{\partial\Psi}{\partial\alpha} = \frac{-\alpha}{(1-\alpha)^2}\sqrt{\frac{1-\alpha}{1+\alpha}}|\tan P|$$

$$\frac{\partial\Psi}{\partial\alpha} = 0 \text{ when } \alpha = 0$$

This suggests the favorable setting of $P\approx\psi$ for maximum sensitivity in $\psi$.

$$-\sin\Delta\frac{\partial\Delta}{\partial\beta} = \frac{1}{\sqrt{1-\alpha^2}}$$

Minimum variation of $$\frac{\partial\Delta}{\partial\beta}$$

at $\sin\Delta=1$

This suggests the preferred setting of the compensator (with retardance $\approx 90°$ to about or substantially $0°$ (that is, to be substantially co-linear with respect to the reference axis) to maximize the sensitivity of the PSCA configuration to the retardance parameter $\Delta$ of the compensator of the set-up.

Embodiments of the Invention in More Detail.

Figure 2:
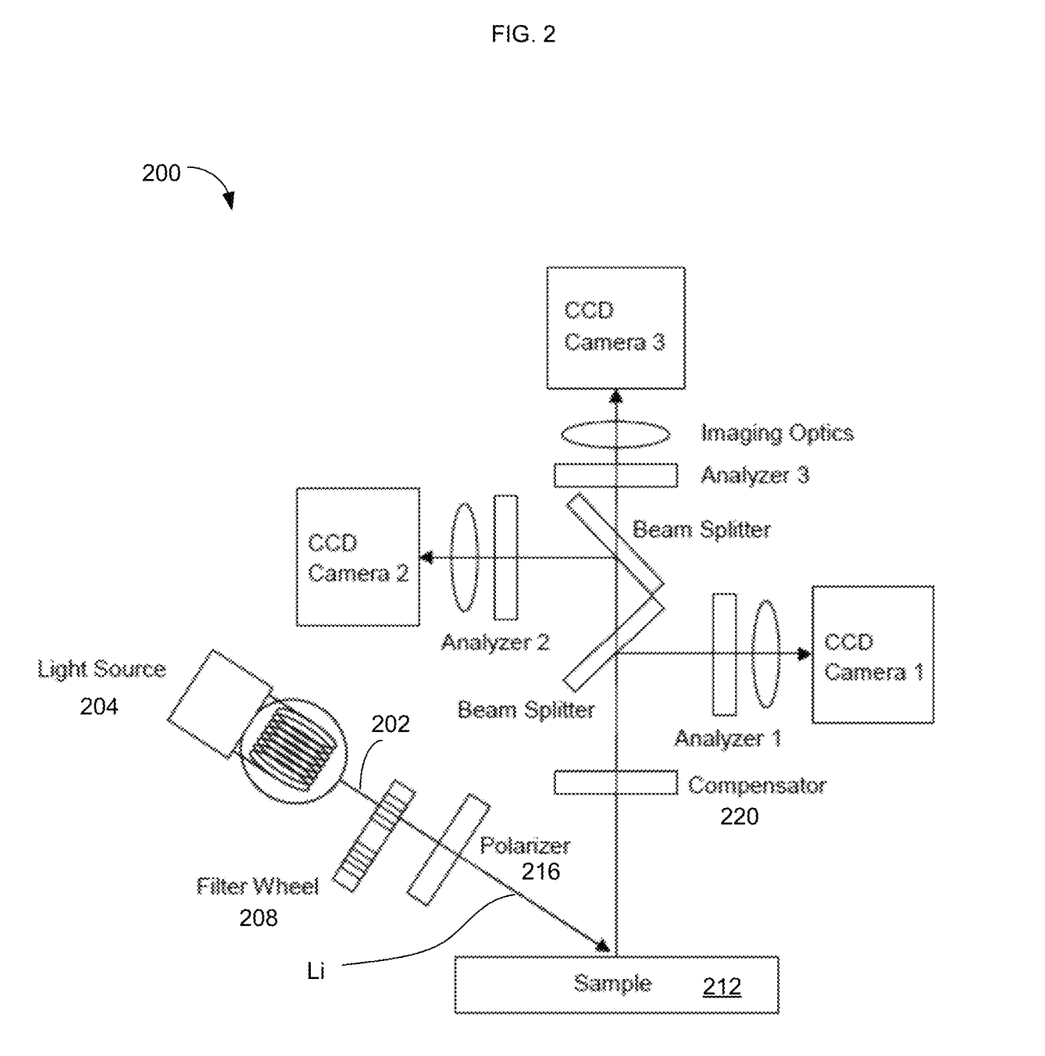
FIG. 2 shows a schematic of a first embodiment of a spectropolarimetric imaging apparatus configured according to an embodiment of the invention.
Figure 3:
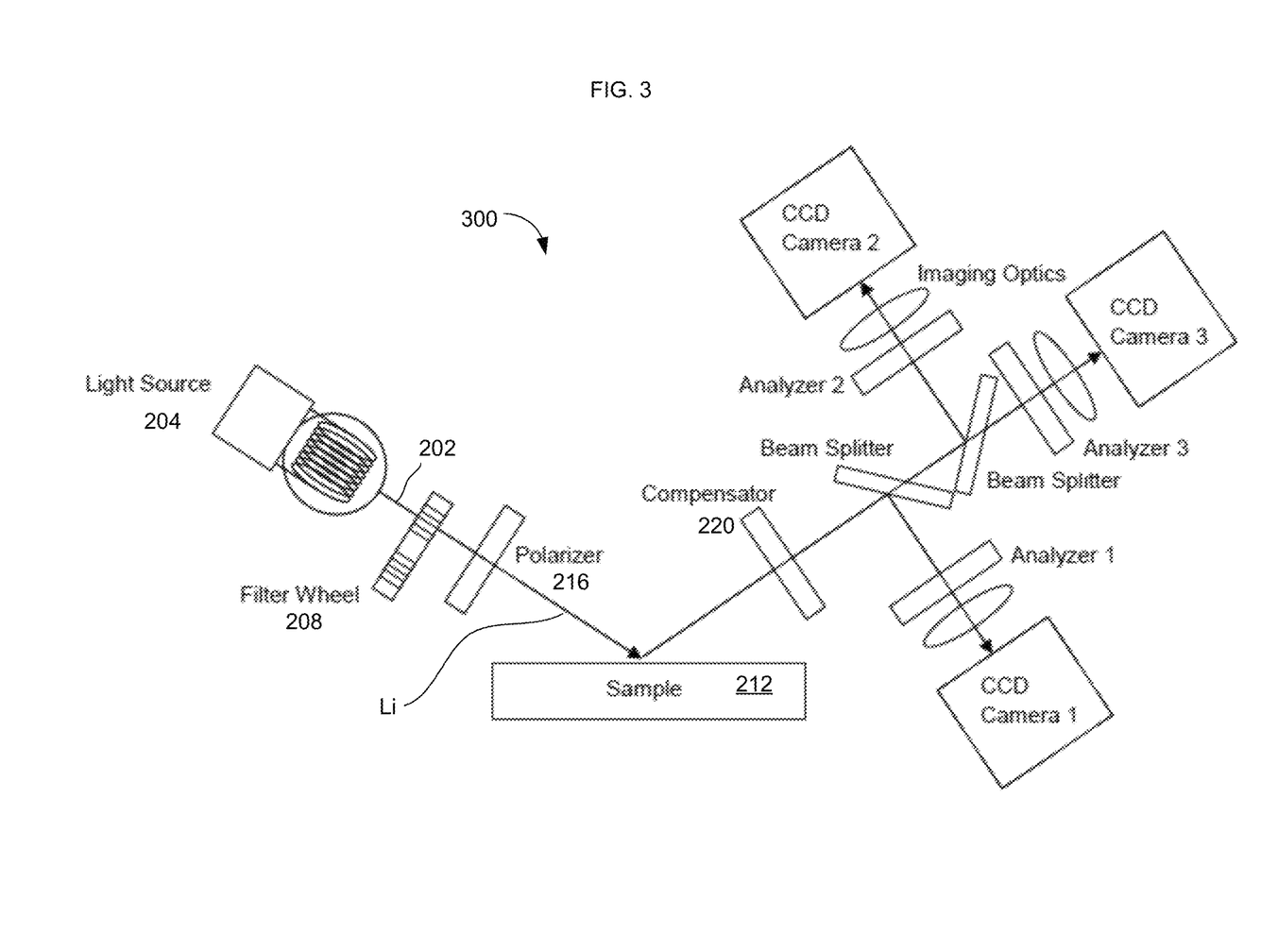
FIG. 3 shows a schematic of a second related embodiment of a spectropolarimetric imaging apparatus.

From the above-presented considerations, several important factors become readily apparent and should be used a guidance for structuring embodiments of the invention, examples of which are depicted in FIGS. 2 and 3.

FIG. 2 shows a schematic of embodiment 200 of a spectropolarimetric imaging apparatus configured to account for non-specular (scattered) reflection of light 202 at the sample 212 to be measured. (In order to mutually re-orient the illumination or light source containing arm and the light-collection or optical detections system containing arm of the apparatus 200, at least one of these arms is equipped with the appropriate repositioner configured to change the angle of incidence of light $L_i$ onto the sample 212 and/or the angle at which light is collected by the LCA from the sample 212. Alternatively or in addition, sample 212—or, preferably, the sample holder in which sample 212 is housed—may be equipped with translational/and/or angular repositioner.) Here, the illumination or light-source containing arm includes a broadband light source 204 that is configured to supply incident light that has spectral content including wavelengths ranging from the UV wavelengths to NIR wavelengths. The illumination arm of the apparatus 200 also includes a filter wheel 208 or an operationally similar variable spectral filter installed to intercept light generated by the source 204 to allow the spectral range of light $L_i$ incident onto the sample 212 to be tuneably defined. In one case, when the measurement of biological samples is intended, the axis of the polarizer 216 of the illumination arm of the apparatus 200 may be set to approximately 21° (generally, from about 18° to about 25°) with respect to the vector of polarization of light 202, which provide increased sensitivity in w. In another case, when the target sample is that of a semiconductor material, the orientation of the of the transmission axis of the polarizer will be set at an angle that is strictly sample dependent, and is within the range from approximately 18 degrees to approximately 25 degrees (in one specific case—at about 21 degrees). The compensator 220 is set to about 0° (which in this context can generally be from about −5° to about +5° to ensure the increased sensitivity in $\Delta$ as discussed above. At the same time, analyzer 1, analyzer 2, and analyzer 3 are set to approximately 0° (generally from about −5° to about +5°, approximately 45° (generally, from about 40° to about 50°, and approximately 90° (generally, from about 85° to about) 95°, relative to the directions of polarizations of incoming beams, respectively. The measurement apparatus 200 is configured to allow the simultaneous collection of the three intensity/irradiance images of the sample 212 (with the use of cameras 1, 2, and 3) that are necessary to generate the w and $\Delta$ images of the sample 212 as different wavelength of incident light.

FIG. 3 illustrates a schematic of another but related embodiment 300 of a spectropolarimetric imaging apparatus configured to operate in specular reflection mode (achieved by the appropriate angular re-orientation between the illumination arm and the light-collection arms of the apparatus, for example). A broadband light source 204 is configured to supply incident light 202 (with spectral content ranging from the UV to NIR) while a filter wheel 208 or equivalent allows the spectral range of light incident onto the sample 212 to be defined. The axis of the polarizer 216 is set to approximately 21° (generally, from about 18° to about 25° with respect to the vector of polarization of light 202, which provide increased sensitivity in w for semiconductor materials and/or biological tissue samples. The compensator 220 is set to about 0° (which in this context can generally be from about −5° to about +5° to ensure the increased sensitivity in $\Delta$, while analyzer 1, analyzer 2, and analyzer 3 are respectively set to approximately 0° (generally from about −5° to about +5°, approximately 45° (generally from about 40° to about 50°, and approximately 90° (generally from about 85° to about 95° relative to the directions of polarizations of incoming beams. The measurement apparatus 300 is configured for the simultaneous collection of the three intensity images (with the use of cameras 1, 2, and 3) that are necessary to generate the $\psi$ and $\Delta$ images of the sample as a function of wavelength of incident light.

The skilled person having the advantage of the preceding discussion will readily appreciate that only three intensity measurements are necessary to compute the ellipsometric parameters $\psi$ and $\Delta$. A beam reflected from the target sample 212 (which may be housed in a dedicated holder device configured to receive at least a portion of polarized light $L_i$ arriving from the source 204) is split into three separate beams with the use of two beam splitter arrangements as shown in FIG. 2 and FIG. 3. For a practical imaging device, the three corresponding intensity images must be acquired substantially simultaneously.

In addition, the preferred orientation of the compensator (to provide retardance of about 90° is set to approximately 0° relative to the axis defining orientations of the cameras while the transmission axes of the three analyzers are set to about 0°, about 45°, and about 90° relative to the polarizations of beams incoming to these analyzers. These configurations allow the determination of $\psi$ and $\Delta$ with only three measurements of intensity for either the specular or non-specular cases. As an additional benefit, setting the compensator to approximately 0° also provides the best sensitivity in $\Delta$.

Moreover, the orientation of the transmission axis of the polarizer 216 is set approximately to the expected value of $\psi$ for the sample under test, in order to provide for the best sensitivity. Since the approximate value of $\psi$ is a known quantity for most materials, this optimum angular orientations for the polarizer 216 can be readily established. For example, the typical refractive index for biological tissue varies from ~1.4 to 1.5 (See: N. Ghosh and I. A. Vitkin, "Tissue polarimetry: concepts, challenges, applications, and outlook," J. Biomed. Opt. 16(11), 110801 (2011).) It follows that the ideal orientation of the polarizer for biological tissue samples will be P≈ψ≈21° relative to the propagation direction of the light for visible wavelengths. In another example, for most commonly used semiconductor materials the refractive index ranges from about 1.46 . . . 1.54 for $SiO_2$ to about 4.69 for PbSe (see, for example, www.researchgate-net/figure/Refractive-indices-of-semiconductors_tb11_236899509, contents of which are incorporated herein by reference). Based on these data, the preferred orientation of the transmission axis of the compensator for investigation of a silica sample (considering n~1.5), for example, will be also about P=ψ≈21°, and for the sample of Ge (averaged refractive index of about 4) P=ψ of about 20°.

Furthermore, multi-spectral polarimetric imaging implemented with the discussed embodiments of the invention now allows for imaging the sample layers at different sample depths to be imaged and provides improved image contrast due to different absorption and scattering characteristics of portions of such samples. And finally, structural ability to vary an angle between the illumination and light-collection arms of the apparatus allows for measurements of both non-specularly (scattered) and specularly reflected light.

The schematics shown in FIGS. 2 and 3 depict the spectropolarimetric imaging apparatus for non-specular (scattered) and specular reflection modes. The two measurement modes can be selected by carrying an angle between the arms of the instrument. A broadband light source supplies incident light from the UV to NIR while a filter wheel or equivalent allows the incident spectral range to be defined. For measurement of the semiconductor materials, the transmission axis of the polarizer 216 is set to a value from about 18° to about 25° (in one specific case—at about 21 degrees), which provides for the improved sensitivity in $\psi$ for semiconductor material samples. The compensator is set to approximately 0° to give the best sensitivity in $\Delta$. Non-polarizing beam splitter arrangements are used to ensure substantially simultaneous imaging of the sample at the same location at each of the three CCD cameras. Each CCD camera is equipped with its own analyzer and imaging optics, thereby forming a respective optical camera sub-system that includes a corresponding polarizer configured as an analyzer, a corresponding lens, and a corresponding optical sensor of the camera. Transmission axes of the analyzer 1, analyzer 2, and analyzer 3 are set to approximately 0°, approximately 45°, and approximately 90° with respect to the axis defined by the state of polarization of light arriving from the compensator 220, respectively, which allows for the simultaneous collection of the three intensity distributions required to determine the ψ and Δ images of the sample as a function of wavelength of incident light $L_i$.

One of the advantages of configuring an embodiment of the invention according to the polarizer-compensator-sample-analyzer (PCSA) design in ellipsometric measurements is that rotating the compensator element 220 improves the signal to noise in the measurement (when compared to a situation in which it is an analyzer or a polarizer that is rotated). Notably, in the proposed imaging polarimeter, the use of three imaging CCD detectors with fixed positions of corresponding analyzers allows the integration time of each detector to be independently set and optimized. Not only does the use of independent CCD detectors greatly improve signal to noise, but this approach allows the removal of the compensator element if desired. Additionally, the angular orientations of the transmission axes of the polarizer and analyzers are fixed, and measurement noise due to uncertainties of the movements/jitter of the polarizer, compensator, and/or analyzer(s) is thus eliminated.

The proposed spectropolarimetric imaging system requires precise alignment of the CCD cameras to avoid loss of ellipsometric image resolution. This can be accomplished mechanically and through software calibration. Precise pixel registration and calibration between the three CCD cameras can be accomplished by aligning to a patterned silicon wafer or equivalent. Additionally, the intensity and linearity of each CCD camera is calibrated using known reflection standards.

Preferred embodiment includes at least one processor adapted to convert pixel intensity data into the $\alpha^2$, β, tan(ψ), and cos(Δ) images referred to in this disclosure. These images preferably may be displayed on an almost real time basis for viewing by system operators. In some applications software can be provided to analyze the image information in an automatic inspection process.

To demonstrate the effectiveness of the imaging spectropolarimeter configured according to the idea of the invention, NIST traceable thickness standards from VLSI Standards, Inc. (VLSI) were measured using the specular reflection mode described in reference to FIG. 3. The NIST traceable thickness standards include a silicon wafer with a patterned thermal oxide of known thickness. The images were measured with illumination at 554 nm, angle of incidence of light onto the sample of about 64°, orientation of the transmission axis of the polarizer at about 45°, and fixed angle sof orientations of the transmission axes of the analyzers of about 0°, about 45°, and about 90°. Because the integration time was optimized for each CCD detector, the compensator element was not required for these measurements. Simulation and analysis of the measured ψ and Δ images was performed using SCI's FilmTek™ software, an optical thin film modeling package based on Abelès 2×2 matrix method (See, for example U.S. Pat. No. 5,889,592, and 5,999,267, the disclosures of which are incorporated herein by reference.)

Figure 4A:
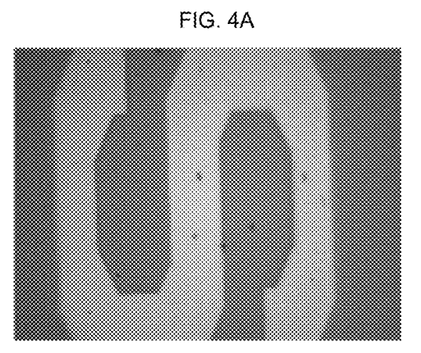
FIG. 4A shows the raw intensity image of a patterned region of an oxide thickness standard.
Figure 4B:
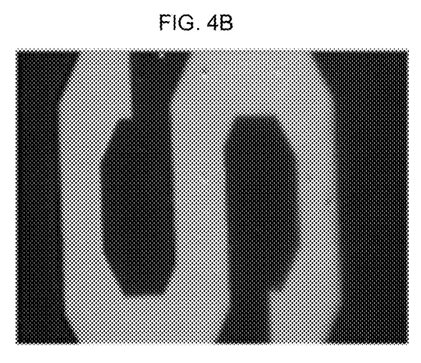
FIGS. 4B, 4C, 4D, and 4E show calculated $\alpha^2$, $\beta$, $\tan(\psi)$, and $\cos(\Delta)$ images.
Figure 4C:
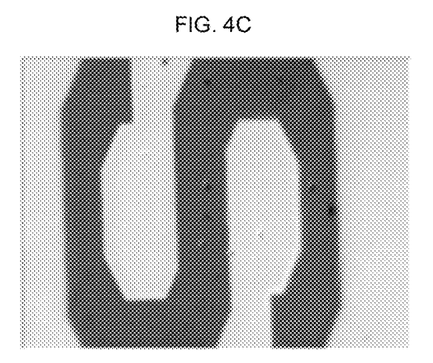
Figure 4D:
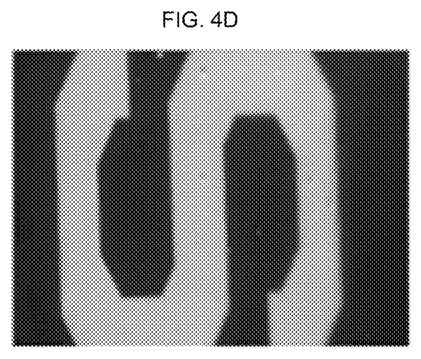
Figure 4E:
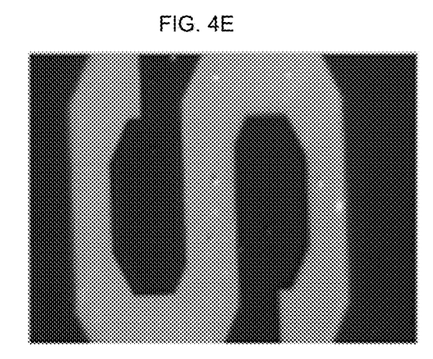

FIG. 4A shows the raw intensity image of a patterned region of the oxide thickness standard (analyzer's axis at about 0°. The camera field of view is approximately 500× 375 microns. The generated (calculated) $\alpha^2$, β, tan(ψ), and cos(Δ) images from the three measurements of light intensity are shown in FIGS. 4B, 4C, 4D, and 4E, respectively. Through etching, the oxide film has been patterned to form indicia resembling letter "S". In the areas surrounding the letter "S", the oxide has been etched away to expose the silicon substrate. The film thickness was then calculated from the measured tan(ψ) and cos(Δ) images using a single layer model with a fixed refractive index of 1.4604, and optical constants of the silicon substrate chosen to match the values used by the National Institute of Standards and Technology. Solving the measured ψ and Δ data for the image region comprising the letter "S" gives an oxide thickness of 524 Angstroms, which is in excellent agreement with the nominal value of 525 Angstroms reported for the standard. The remaining oxide thickness for the "bare" silicon region is calculated to be 82.8 Angstroms from the images, which is in good agreement with spectroscopic ellipsometric measurements of the sample using a calibrated instrument.

Figure 5A:
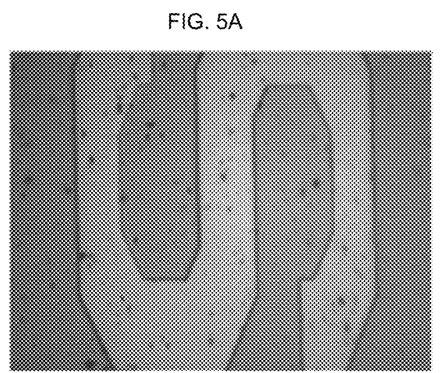
FIG. 5A shows a raw intensity of a patterned region of a different VLSI oxide thickness standard.
Figure 5B:
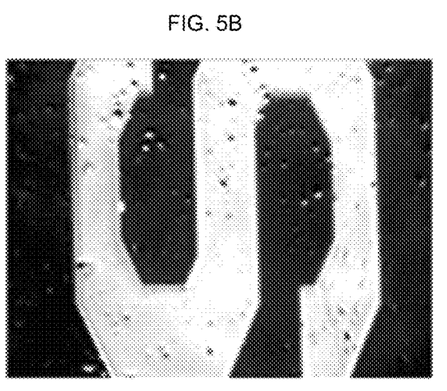
FIGS. 5B, 5C, 5D, and 5E present assessed $\alpha^2$, $\beta$, $\tan(\psi)$, and $\cos(\Delta)$ images.
Figure 5C:
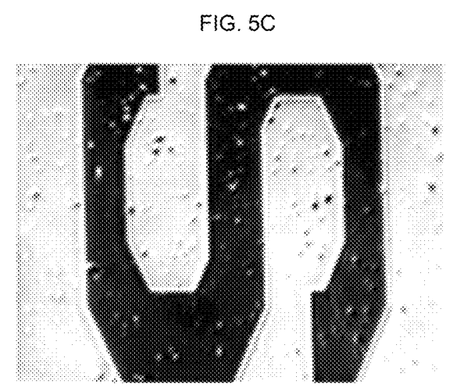
Figure 5D:
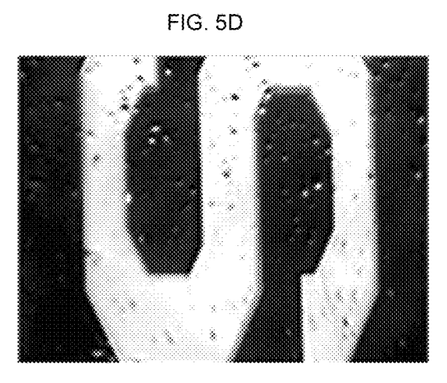
Figure 5E:
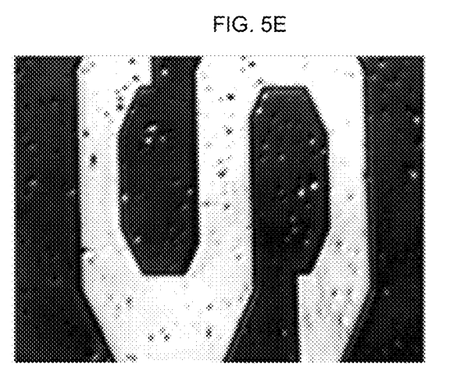

Similarly, FIG. 5A shows the raw intensity image of a patterned region of a different VLSI oxide thickness standard (analyzer's transmission axis at about 0°, acquired with an embodiment of the invention. The calculated $\alpha^2$, β, tan(ψ), and cos(Δ) images from the three intensity images are shown in FIGS. 5B, 5C, 5D, and 5E, respectively. Solving the measured w and A data for the image region containing the indicia resembling the letter "S" established the oxide layer thickness of 6920 Angstroms, which is in excellent agreement with the nominal value of 6915 Angstroms reported for the standard. The remaining oxide thickness for the "bare" silicon region is calculated to be 60.0 Angstroms from these images, which is in good agreement with spectroscopic ellipsometric measurements of the sample using a calibrated instrument. The measured oxide layer thicknesses obtained from the images of the patterned VLSI thickness standards demonstrates the quantitative sensitivity and accuracy of the invention. The use of the embodiment of the invention demonstrates a stark advantage of the proposed measurement methodology: although all patterned oxide samples can, of course, be visualized in the raw intensity image (FIG. 5A) in light with a given polarization or even in unpolarized light, the oxide thicknesses simply cannot be numerically determined from observation of the raw intensity image of FIG. 5A.

Figure 6A:
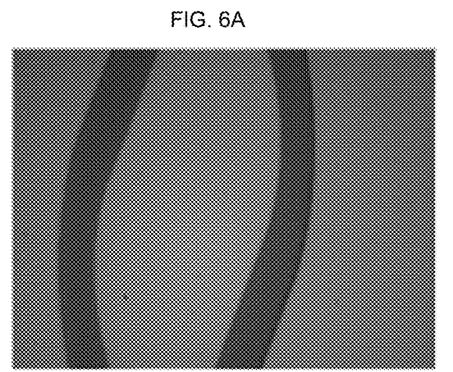
FIG. 6A shows the raw intensity image of a patterned region of an oxide thickness standard.
Figure 6B:
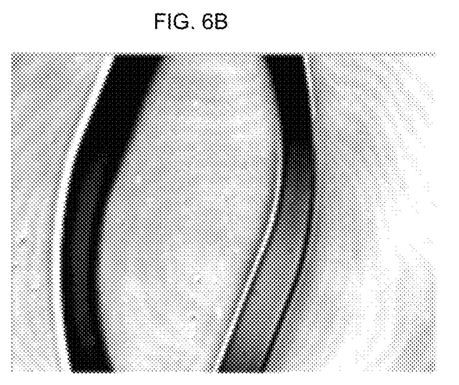
FIGS. 6B, 6C, 6D, and 6E show assessed $\alpha^2$, $\beta$, $\tan(\psi)$, and $\cos(\Delta)$ images.
Figure 6C:
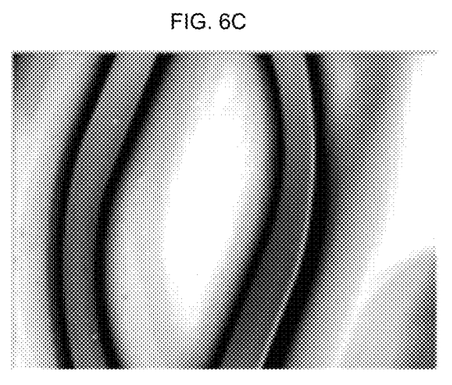
Figure 6D:
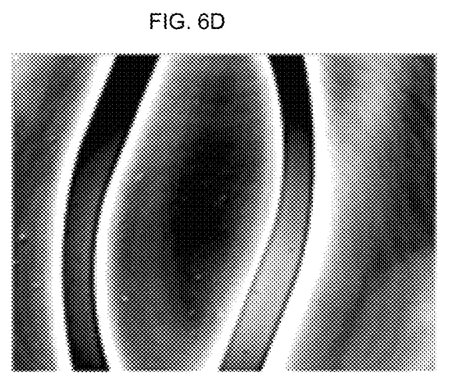
Figure 6E:
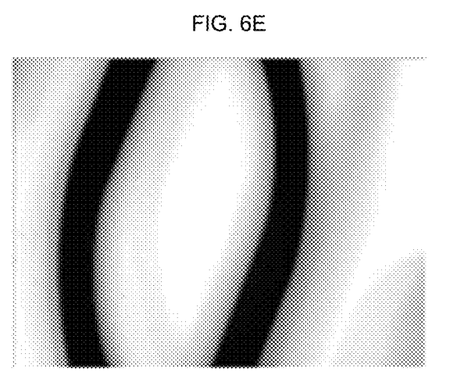
Figure 7A:
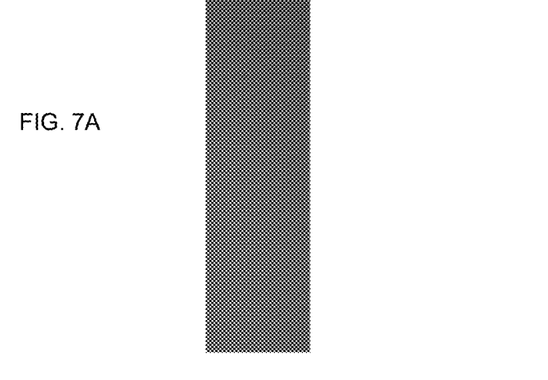
FIGS. 7A, 7B, 7C, 7D, and 7E show identified regions of interest of images of FIGS. 6A through 6E, respectively.
Figure 7B:
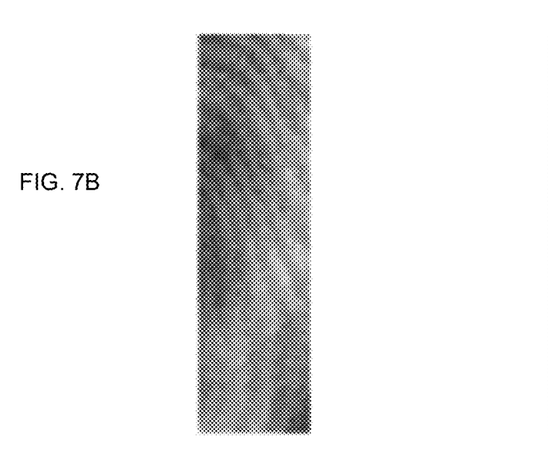
Figure 7C:
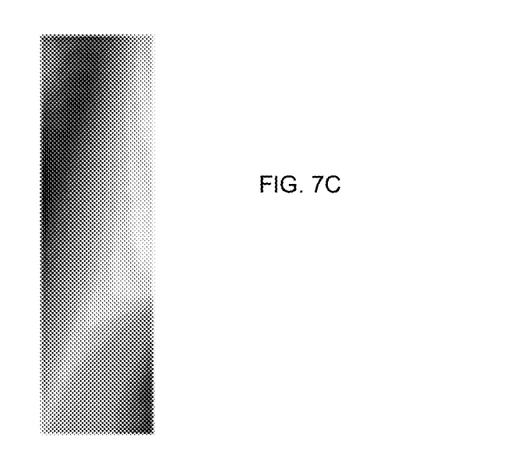
Figure 7D:
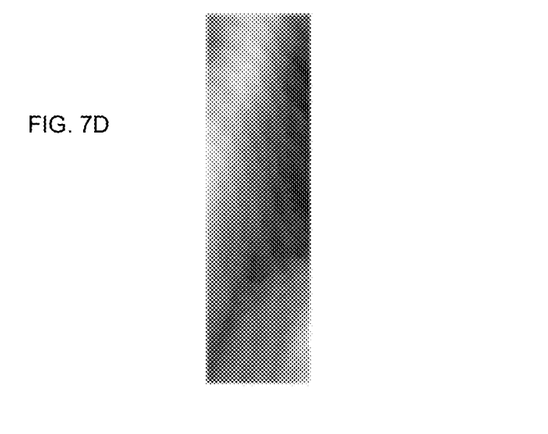
Figure 7E:
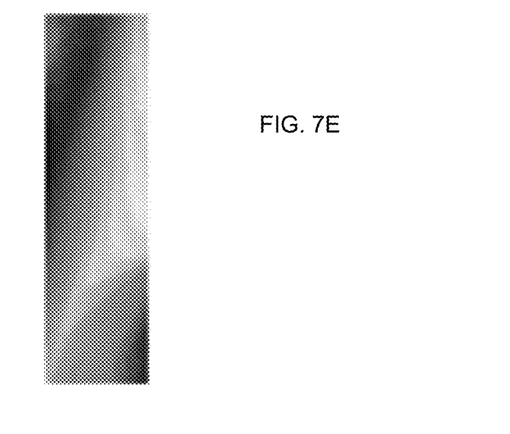

To demonstrate the capability of an embodiment of the invention to enhance contrast and resolve features not otherwise observable in a raw intensity image (FIG. 4A, FIG. 5A), a sample that contained a very small thickness gradient surrounding the pattern of interest was also imaged. Similar to the VLSI thickness standards, the sample included a silicon wafer with a thermal oxide film thereon. Patterned regions were obtained by etching away the oxide film. FIG. 6A illustrates the raw intensity image of a patterned region of the oxide sample (transmission axis of the analyzer at about 0° representing indicia resembling letter "O". The generated $\alpha^2$, β, tan(ψ), and cos(Δ) images from the three intensity images are shown in FIGS. 6B, 6C, 6D, and 6E, respectively. Solving the empirically-acquired w and A data for the image region containing the letter "O" resulted in an oxide thickness of 226 Angstroms. The average oxide thickness for the region surrounding the indicia "O" was calculated to be 1262 Angstroms from the images.

Of particular interest were the regions adjacent to (on the right-hand side of) the patterned indicia "O" (shown, for each of images of FIGS. 6A through 6E, in corresponding FIGS. 7A, 7B, 7C, 7D, and 7E). The etching process produced a gradient of thickness of the remaining oxide layer. Although this gradient is not observable in the raw intensity image (FIG. 7A), it can be easily seen in the calculated $\alpha^2$, $\beta$, $\tan(\psi)$, and $\cos(\Delta)$ images of FIGS. 7B through 7E). The measured oxide thickness ranged from 1267 to 1286 Angstroms. From the $\tan(\psi)$ of FIG. 7E, an oxide thickness gradient of 19 Angstroms could be easily resolved and readily visualized without additional calculations. The images produced with the use of embodiments of the invention clearly demonstrate the potential for resolving those image features in the spectropolarimetric images that are not observable in a raw intensity image of the sample.

One of the stark practical advantages provided by implementation of an embodiment of the invention is the ease of image interpretation. Unlike the Mueller matrix images, the measured $\alpha^2$, $\beta$, $\tan(\psi)$, and $\cos(\Delta)$ in combination with the raw intensity images can be viewed in real time by a physician or a technician and not require further mathematical or computer analyses for interpretation. This is essential both in the clinical setting (where imaging-based management decisions are ideally made at the point-of-care based on the real-time analysis of a biological sample) and under the limitations imposed by the semiconductor manufacture and processing. The present invention provides a measurement system and method for fast spectropolarimetric imaging for performing tissue diagnostics in situ, in vivo, and in real time. The system design has the potential for compactness and miniaturization to allow for remote, hand held use. The real time output of ellipsometric w and A images provides additional information content for improved contrast and higher resolution imaging of tissue and its underlying structure for increased discrimination between benign and malignant tissues. Although the primary application is for non-invasive biomedical diagnostics, the invention could have applications in many fields of optical metrology ranging from remote sensing to industrial monitoring.

The above discussed embodiments are examples of embodiments of the present invention and are not to be considered as exclusive in any sense. Persons skilled in this art will recognize that many modifications and additions can be applied within the general concepts of the present invention including many of the features discussed in the documents cited in the Background section of this application. For example, targets could include an extremely wide variety of targets from tiny integrated circuits to battlefield targets. The polarized light sources could include a white light source, a filter and a polarizer or one of many commercially available laser light sources. Various devices could be adapted to perform as intensity analyzers, including fixed grating linear CCD or 2D CCD detector arrays. The polarizer can be set at angles other than about 21° depending on the optical properties of the target, but normally the angle will be between 0 and 90 degrees. Embodiments of the present invention may be applied in a large variety of applications including the following applications: a) Medical applications—for example, as systems specifically configured for cancer detection and screening; b) Semiconductor industry—for example, as material characterization apparatus configured to defect inspection, film thickness, and material characterization (surface roughness, refractive index, chemical composition and containing an embodiment of the imaging spectropolarimeter discussed above; c) Defense applications (for example, remote sensing and enhanced imaging processes).

A variety of light sources could be used, for example: broadband, laser diode, LED, etc. While a black and white (grayscale) CCD camera was assumed in the above discussion for performing intensity/irradiance measurements, a color CCD camera(s) can be interchangeably employed in order to acquire spectroscopic intensity information (for example, within red, green, and/or blue regions of the visible spectrum). In addition to CCD cameras, light intensity could be detected with fixed grating spectrometers with linear or 2D CCD arrays to give spectroscopic intensity measurements. The field of view of the overall system can be controlled by employing zoom lenses instead of lenses with fixed focal lengths. This allows the spatial resolution of the images to go down to micron resolution for semiconductor applications.

Whether explicitly stated or not, and whether expressly so indicated in the Drawings, embodiments of the apparatus of the invention include an optionally-programmable processor (microprocessor) and/or dedicated electronic circuitry controlled by instructions stored in a memory. The memory may be random access memory (RAM), read-only memory (ROM), flash memory or any other memory, or combination thereof, suitable for storing control software or other instructions and data. Some of the functions performed by such electronic circuitry/processor are those governing the operation of the apparatus and defining the processing regimes; and acquisition of processing data representing such operation and measurement data. Those skilled in the art should readily appreciate that such functions may be implemented as computer program instructions, software, hardware, firmware or combinations thereof. Those skilled in the art should also readily appreciate that instructions or programs defining the functions of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

For the purposes of this disclosure and the appended claims, the use of the terms "substantially", "approximately", "about" and similar terms in reference to a descriptor of a value, element, property or characteristic at hand is intended to emphasize that the value, element, property, or characteristic referred to, while not necessarily being exactly as stated, would nevertheless be considered, for practical purposes, as stated by a person of skill in the art. These terms, as applied to a specified characteristic or quality descriptor means "mostly", "mainly", "considerably", "by and large", "essentially", "to great or significant extent", "largely but not necessarily wholly the same" such as to reasonably denote language of approximation and describe the specified characteristic or descriptor so that its scope would be understood by a person of ordinary skill in the art. In one specific case, the terms "approximately", "substantially", and "about", when used in reference to a numerical value, represent a range of plus or minus 20% with respect to the specified value, more preferably plus or minus 10%, even more preferably plus or minus 5%, most preferably plus or minus 2% with respect to the specified value. As a non-limiting example, two values being "substantially equal" to one another implies that the difference between the two values may be within the range of +/−20% of the value itself, preferably within the +/−10% range of the value itself, more preferably within the range of +/−5% of the value itself, and even more preferably within the range of +/−2% or less of the value itself The use of these terms in describing a chosen characteristic or concept neither implies nor provides any basis for indefiniteness and for adding a numerical limitation to the specified characteristic or descriptor. As understood by a skilled artisan, the practical deviation of the exact value or characteristic of such value, element, or property from that stated falls and may vary within a numerical range defined by an experimental measurement error that is typical when using a measurement method accepted in the art for such purposes.

While the invention is described through the above-described exemplary embodiments, it will be understood by those of ordinary skill in the art that modifications to, and variations of, the illustrated embodiments may be made without departing from the inventive concepts disclosed herein. Furthermore, disclosed aspects, or portions of these aspects, may be combined in ways not listed above. Accordingly, the invention should not be viewed as being limited to the disclosed embodiment(s).

The invention claimed is:

1. A material characterization apparatus comprising:
   (i) a holder device configured to house material contents therein;
   (ii) an imaging spectropolarimeter that includes:
      a light source configured to generate polarized light, said light source including an optical spectral filter configured to define a desired spectral range of said polarized light and a source polarizer having a transmission axis thereof oriented at a polarizer angle with respect to a chosen axis, wherein the polarizer angle is defined within a range from about 18° to about 25° and is necessarily dependent on a refraction index of the material contents;
      an optical detection system including:
         a first optical camera sub-system comprising a first camera polarizer configured to have a first transmission axis thereof to be substantially co-linear with the chosen axis, a first lens, and a first optical sensor,
         a second optical sub-system comprising a second camera polarizer configured to have a second transmission axis thereof to be tilted by substantially 45° to said chosen axis, a second lens, and a second optical sensor,
         a third optical camera sub-system comprising a third camera polarizer configured to have a third transmission axis thereof to be at substantially 90° with respect to said chosen axis, a third lens, and a third optical sensor;
      and
         an optical delivery system configured to receive at least a portion of said polarized light and to redirect light from the at least a portion of said polarized light to each of the first, second, and third optical camera units sub-systems; and
   (iii) a programmable electronic circuitry operably connected to the optical detection system and a computer usable tangible non-transitory storage medium, said storage medium having computer readable program code thereon, the computer readable program code including:
      program code for acquiring first, second, and third optical data respectively representing first, second, and third spatial distributions of intensities of portions of the light received respectively by the first, second, and third optical sensors; and
      program code for generating, based on said first, second, and third optical data, first, second, and third polarimetric images of the material contents of the holder;
   wherein the holder device is disposed in optical communication with the light source and the optical delivery system;
   wherein the material characterization apparatus is configured to acquire the first, second, and third optical data substantially simultaneously and/or generate the first, second, and third polarimetric images substantially simultaneously, and
   wherein said material characterization apparatus is configured as a non-invasive biomedical diagnostic system or as a semiconductor material inspection system.

2. A material characterization apparatus according to claim 1, wherein:
   (2A) when the material characterization apparatus is configured as the non-invasive biomedical diagnostic system, the material contents of the holder device include a biological tissue, and the program code for generating includes program code for generating images representing cancer detection and/or screening in said biological tissue; or
   (2B) when the material characterization apparatus is configured as a semiconductor material inspection system, the material contents of the holder device include a semiconductor material, and the program code for generating includes program code for generating an image representing a structural defect and/or a geometrical parameter and/or a material content of said semiconductor material.

3. A material characterization apparatus according to claim 1, wherein the light source is configured to generate a broadband light having a spectral bandwidth including UV light, visible light, and IR light.

4. A material characterization apparatus according to claim 1, further comprising:
   a repositioning system configured to mutually reposition the light source and the optical detection system to have the optical detection system acquire light contained
   (4A) only in a specular reflection of the polarized light originated at the material contents of the holder device, or
   (4B) only in a non-specular reflection of the polarized light originated at the material contents of the holder device.

5. A material characterization apparatus according to claim 1, wherein the imaging spectropolarimeter includes a zoom lens at at least one of the first, second, and third optical camera sub-systems, said zoom lens being configured to change a field of view perceived by a respective optical sensor.

6. A material characterization apparatus according to claim 5, wherein the zoom lens is configured to define a spatial resolution of said first, second, and third polarimetric images to be a micron-scale resolution.

7. A material characterization apparatus according to claim 1, wherein the optical delivery system includes first and second optical beam splitters and/or the optical detection system is a three-camera optical detection system.

8. A material characterization apparatus according to claim 1, wherein the programmable electronic circuitry is configured to convert pixel intensity data received from the first, second, and third optical sensors into at least four sets of images for each type of the material contents of the holder device.

9. A method comprising:
using the material characterization apparatus according to claim 1;
receiving polarized light, delivered from the light source of the apparatus, at the material contents of the holder device of the apparatus, wherein said material contents include a semiconductor material;
substantially simultaneously acquiring light, which has interacted with the material contents of the holder device and which has been redirected to the optical detection system only specularly or only non-specularly, at each of the first, second, and third optical sensors; and
with the use of the programmable electronic circuitry of the apparatus, generating first, second, and third polarimetric images of said semiconductor material, wherein each of the first, second, and third polarimetric images contains data representing at least one of a structural defect, a geometrical parameter, and a material composition of said semiconductor material.

10. A method according to claim 9, further comprising:
varying a field of view subtended by at least one of the first, second, and third optical sensors of the material characterization apparatus to define a spatial resolution of a corresponding one of the first, second, and third polarimetric images to be a micron-scale resolution.

11. A method according to claim 9, further comprising: converting pixel intensity data received from the first, second, and third optical sensors into at least four sets of images of said semiconductor material.

* * * * *